United States Patent [19]
Corbin et al.

[11] Patent Number: 5,977,193
[45] Date of Patent: *Nov. 2, 1999

[54] RECLAIMING EPSILON-CAPROLACTAM FROM NYLON 6 CARPET

[75] Inventors: Thomas F. Corbin; Alan C. Handermann, both of Asheville; Richard Kotek, Arden; William D. Porter, Asheville; Jack A. Dellinger, Weaverville; Edward A. Davis, Candler, all of N.C.

[73] Assignee: BASF Corporation, Parsippany, N.J.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 07/943,795

[22] Filed: Sep. 11, 1992

Related U.S. Application Data

[63] Continuation-in-part of application No. 07/718,720, Jun. 21, 1991, Pat. No. 5,169,870.

[51] Int. Cl.$^6$ ................................ C08J 11/14; C08J 11/16
[52] U.S. Cl. ....................... 521/49.8; 521/40.5; 523/129; 528/487; 525/419
[58] Field of Search ................................. 521/49.8, 40.5; 525/419; 528/487; 523/129

[56] References Cited

U.S. PATENT DOCUMENTS 5,169,870  12/1992  Corbin et al. ........................... 521/49.8

*Primary Examiner*—Andrew E. C. Merriam

[57] ABSTRACT

$\epsilon$-Caprolactam is continuously recovered from carpet made from nylon 6 face fibers and a backing. The carpet is fed to a separator to prepare scrap containing nylon 6 and auxiliary materials. The scrap from the separator is fed to a depolymerizing reactor to produce an $\epsilon$-caprolactam containing distillate and more auxiliary materials. The $\epsilon$-caprolactam in the distillate is separated from other volatiles and purified. The auxiliary materials are also recovered or re-used.

14 Claims, 3 Drawing Sheets

RECLAIMING EPSILON-CAPROLACTAM FROM NYLON 6 CARPET

RELATED APPLICATIONS

This application is a continuation-in-part application of U.S. patent application Ser. No. 07/718,720, filed Jun. 21, 1991, now U.S. Pat. No. 5,169,870.

FIELD OF THE INVENTION

The present invention relates to a process for reclaiming ε-caprolactam. More particularly, the present invention relates to a process for reclaiming ε-caprolactam from nylon 6 carpet.

BACKGROUND OF THE INVENTION

As used herein, the term "auxiliary stream" refers to a stream generated during the recovery of ε-caprolactam which does not contain primarily ε-caprolactam or poly ε-caprolactam.

As landfills continue to reach capacity, raw materials are depleted, and man recognizes that the earth's resources are limited, more and more materials are recycled. Synthetic polymers have long presented problems in recycling due to their often being commingled with other materials and to sometimes apparently irreversible polymerization from which useful raw materials cannot be easily obtained.

Certain polyamides, however, are known to be hydrolytically convertible to monomers which can be re-used. Especially in the case of nylon 6, the monomeric starting materials are reclaimed from waste polymer and used in the manufacture of man-made fibers. The literature reveals procedures for reclaiming such monomers and polymers. L. A. Dmitrieva et al., Regeneration of ε-Caprolactam from Wastes in the Manufacture of Polycaproamide Fibres and Yarns, *Fibre Chemistry*, March 1986, pp. 229–241, describes methods for reclaiming polycaprolactam (nylon 6) waste.

There are generally two methods for reclaiming nylon 6 waste. The first involves reprocessing the waste nylon 6, for example, via remelting and extrusion, to form useful articles. This concept is demonstrated in U.S. Pat. No. 4,143,001 to Raab et al.

The second method involves chemical regeneration through depolymerization. Processes for depolymerizing solid polyamide waste are known. For example, U.S. Pat. No. 2,343,174 to Edison et al. shows general hydrolytic depolymerization using steam. U.S. Pat. No. 3,988,406 to Nakamura et al. shows the recycling of polyamide waste by thermal depolymerization.

Among the polyamides depolymerized for re-use of the monomer is nylon 6. For example, U.S. Pat. No. 4,107,160 to Dicoi et al. describes reclamation of solid nylon 6 waste (generated during the processing of nylon 6), low molecular weight oligomers and residual monomer from the polycondensation of caprolactam.

Other polymers are also recycled. An example of a process for continuously degrading various plastics is provided in U.S. Pat. No. 4,051,212 to Grigat et al. Grigat et al. shows a process for continuously hydrolytically degrading plastics. The hydrolyzable material is introduced with water into a screw machine, where it is subjected to a temperature of 100° C. to 300° C. at a pressure of 5 to 100 bars for 2 to 100 minutes.

Although the motivation for reclaiming raw materials from waste polymer or spent polymeric products is well recognized, some products do not readily lend themselves to recycling. Items which are composites of several materials present problems. Along these lines, polymeric materials formed into carpets present an interesting reclamation problem. This is due, in part, to the variety of materials present in traditional carpet and the manner in which they are intimately connected. In traditional carpets, the tufts are often nylon 6, while the backing of a nylon 6 tufted carpet may include jute, polypropylene and latex, among other things. Also, the latex may contain fillers such as calcium carbonate, clay or aluminum trihydrate. The chemical and physical nature of these materials is such that reclamation of ε-caprolactam from nylon 6 carpets has traditionally been considered too complex, too expensive and too cumbersome to be practical.

Traditional thought was that polypropylene or jute and especially latex would generate impurities which would make purification so difficult or the reclaimed yield so low as to render depolymerization of carpets impractical. Moreover, the $CaCO_3$ usually present in the latex as filler would neutralize an equivalent amount of any acid depolymerization catalyst, such as $H_3PO_4$.

In addition, many recycling schemes focus on a single ingredient in a mixed waste stream, leaving the remaining ingredients for landfilling, incineration, etc. Yet, the more portions of mixed waste that can be regenerated to materials having another useful life, the more valuable, economically and environmentally, is the process.

SUMMARY OF THE INVENTION

Accordingly, the present invention is a process for recovering ε-caprolactam from carpet having nylon 6 face fibers and backing containing one or more non-nylon 6 materials such as polypropylene, jute, latex, dyestuffs, pigments and fillers. The carpet is provided to a mechanical separator to prepare scrap containing both nylon 6 and non-nylon 6 backing materials, and a first auxiliary stream. The scrap from the separator is fed to a depolymerization reactor to produce an ε-caprolactam containing distillate and a second auxiliary stream. ε-Caprolactam in the distillate is separated from other volatiles and then purified so that the ε-caprolactam is of sufficient purity for reuse as a starting material for nylon 6 intended for use in carpet fiber. Auxiliary streams are also recycled.

It is an object of the present invention to reclaim ε-caprolactam from carpets containing nylon 6.

Another object of the present invention is to re-use auxiliary streams generated from reclaiming e-caprolactam from carpets containing nylon 6.

Related objects and advantages will be readily apparent to one ordinarily skilled in the art after considering the following.

DESCRIPTION OF THE PREFERRED EMBODIMENTS

To promote an understanding of the principles of the present invention, descriptions of specific embodiments of the invention follow, and specific language describes the same. It will nevertheless be understood that no limitation of the scope of the invention is thereby intended, and that such alterations and further modifications, and such further applications of the principles of the invention as discussed are contemplated, as would normally occur to one ordinarily skilled in the art to which the invention pertains.

The present invention is a process for recovering ε-caprolactam from scrap or post-consumer carpeting. Such carpeting is a composite of many materials, such as latex, polypropylene, jute, fillers, finishes, soil, etc. Additional facets of the present invention are steps for recovering and re-using secondary materials which are generated as auxiliary streams.

The present invention surprisingly produces from nylon 6 carpets ε-caprolactam which contains substantially no impurities other than those derived from nylon 6. Although it is preferred that most of the polypropylene and latex or other non-nylon materials are separated by mechanical means, it is not essential. Where mechanical means are used, there is much less by-product from depolymerization, and the reclamation of ε-caprolactam is easier.

Figure 1:
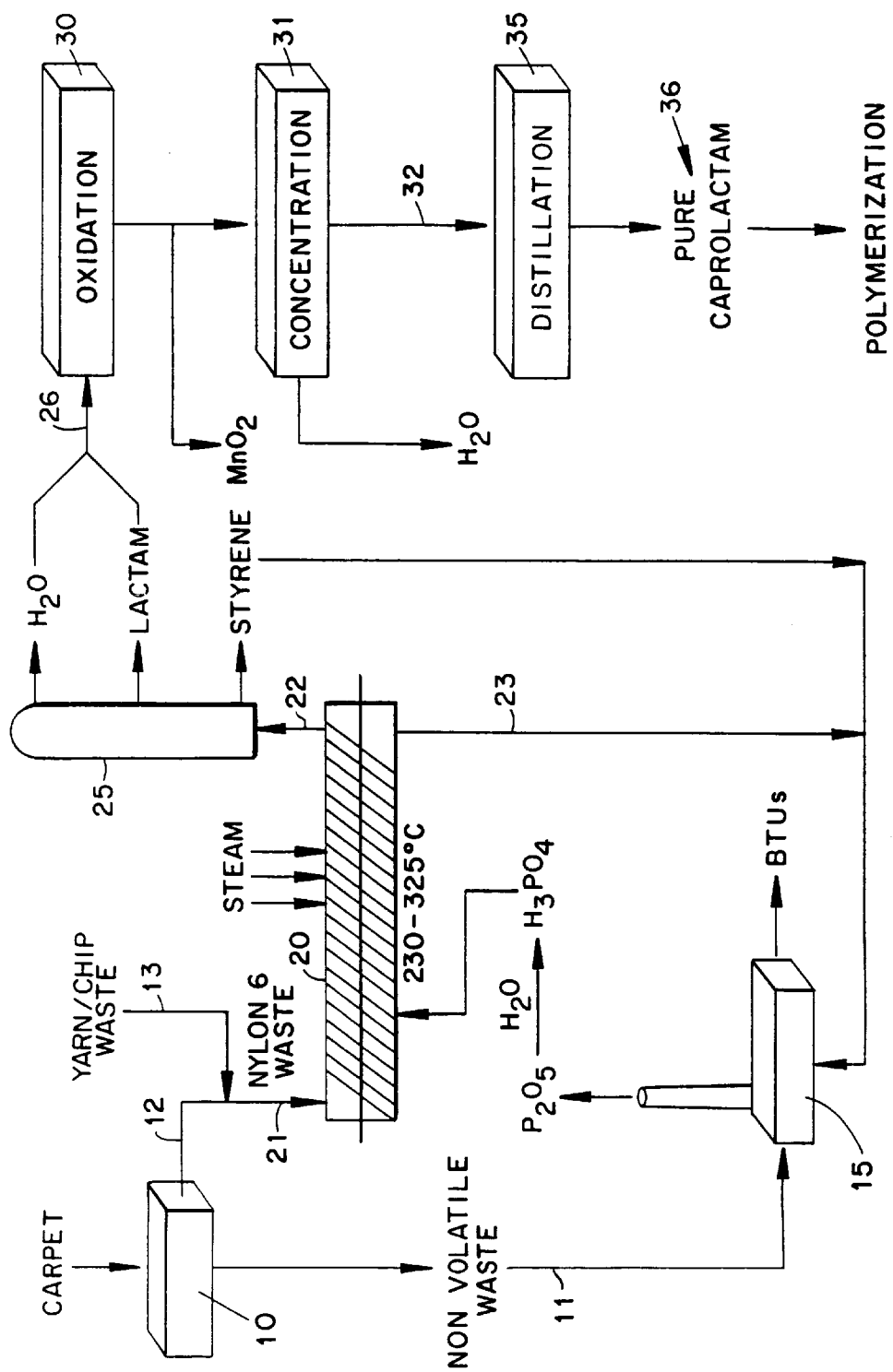
FIG. 1 is a schematic of the process of the present invention.

The process of the present invention is schematically illustrated in FIG. 1. In the first step, carpet in strips or pieces is fed to separator 10 in which the carpet is mechanically reduced to a smaller size, preferably via a shredder or grinder. A large portion of any non-caprolactam materials, including latex, jute and polypropylene may be separated using an air classifier or any other mechanical action. Of course, those skilled in the art will readily understand that the term "mechanical" refers to separations which are more physical in nature rather than separations which are more chemical in nature. For example, hot air knife, hot wire, electrostatic separation, wet separation, flotation, etc., may be used. Nonvolatile auxiliary stream 11 removed in separator 10 may be routed away and may, optionally, be directed to power house 15. At power house 15, the auxiliary stream is used to produce energy. Several exemplary separator components suitable for use in the present invention are available from Schirp Corporation as Type 75, Type 38CIII, Type 58, Type 38CII, Type 66, Type 71, Type 66-L, Type 57, Type 57S500, Type 64, and Type 62C.

Figure 2:
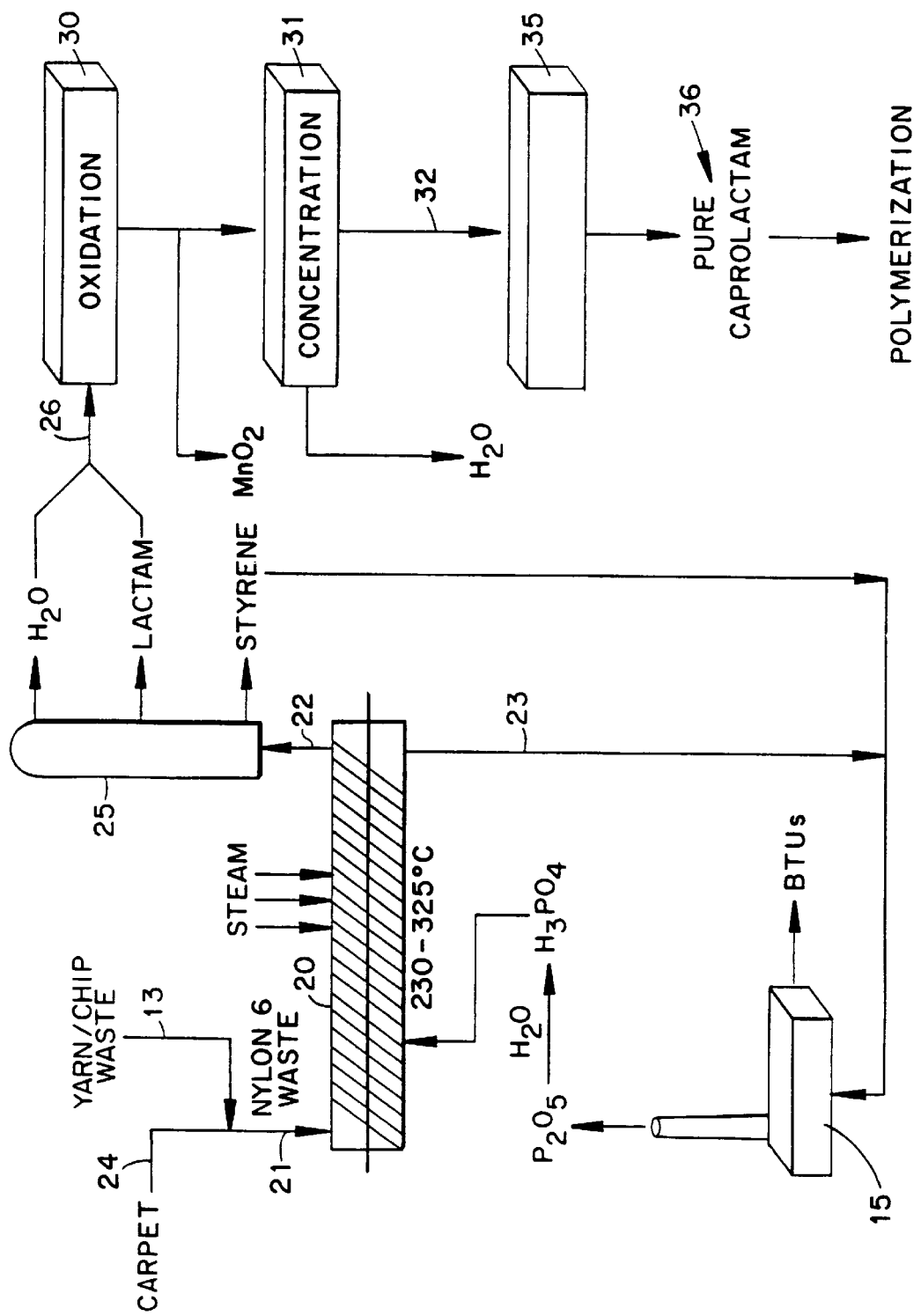
FIG. 2 is a schematic of an alternate process of the present invention.

Nylon 6 (12) obtained from separator 10 is then fed to a continuous depolymerization reactor (CDR) unit 20. An evaporator can be used for depolymerization. LIST, Inc. (40 Nagog Park, Acton, Mass. 01720) is one source for such evaporators. It is also possible to feed carpet directly to the CDR, bypassing the separator step. This is shown in FIG. 2, where carpet 24 is fed directly to unit 20, optionally after combination with solid waste 13. The rest of the process is substantially as shown in FIG. 1, so that the reference numbers are the same.

The following description of depolymerization relates to a CDR. However, the continuous depolymerization process can be carried out with a batch reactor or a semi-continuous reactor. The continuous reactor is preferred mostly because the process does not have to be interrupted to remove non-volatile reactor bottoms. Also, the following description of depolymerization relates to one possible procedure. Other known depolymerization methods are also suitable. For example, non-catalytic methods such as those described in U.S. Pat. No. 4,620,032 to Doerr and U.S. Pat. No. 4,605,762 to Mandoki are suitable. Also, an article entitled "Depolymerization of Poly-ε-caprolactam Catalyzed by Sodium Hydroxide", authored by A. K. Mukherjee and D. K. Goel in *JOURNAL OF APPLIED SCIENCE*, Vol. 22, 361–368 (1978) describes a depolymerization catalyzed by sodium hydroxide which could be used.

Optionally, other nylon 6 solid waste (13), such as yarn waste, chip waste or extruder slag, can be combined with the nylon 6 feed from separator 10 or with the carpet if the separator is not used. Also, optionally, contaminated monomeric caprolactam or caprolactam oligomers, such as from nylon 6 wash water, can be fed to depolymerization unit 20. If an evaporator is used as the CDR, then preferably the waste carpet material is molten prior to feeding into the evaporator. Total waste feed 21 is fed through depolymerization unit 20. One preferred manner of feeding waste 21 is by means of an auger inside CDR unit 20, but other means for feeding the waste, such as a conveyor belt or gravity feed, should be readily apparent.

In CDR unit 20, a depolymerization catalyst is injected downstream from where waste 21 is fed into depolymerization unit 20. However, it is preferred to add the catalyst earlier, for example, together with waste 21. One suitable depolymerization catalyst is phosphoric acid, which is preferably provided at a rate to make the acid concentration in the reactor from 1%–20%, more preferably from 5%–15%, still more preferably, 5–15% more than that required to neutralize any residual $CaCO_3$ present. Excess phosphoric acid can be recovered via the reactor waste. Other depolymerization catalysts can also be used, such as boric acid and phosphate salts.

Superheated steam, preferably between about 100° C. to about 450° C., is provided to CDR unit 20. Preferably, the steam is provided further downstream than the depolymerization catalyst to help distill lactam volatiles as they are formed. It may be added at a rate to generate a distillate having a lactam concentration up to about 90%. But more or less steam can be added, depending on the amount of auxiliary heat added to the CDR by other means, e.g., hot oil or electrical resistance heat to the wall of the CDR.

The depolymerization reactor is preferably maintained at a temperature between about 230° C. and about 325° C., more preferably between about 250° C. to 280° C. The superheated steam volatilizes caprolactam and other volatile compounds out of the melt, as these compounds are formed to produce distillate 22.

Distillate 22 is then passed through fractionating column 25, where water and caprolactam are fractionated from other non-aqueous volatile substances, for example, styrene. Non-volatile residue (auxiliary stream) 23 from CDR unit 20 may, optionally, be routed as an auxiliary stream to power house 15 as a further fuel supply. Styrene produced from fractionating styrene and other non-aqueous volatile distillates from water and aqueous distillates such as ε-caprolactam from the aqueous lactam are optionally routed to power house 15 for fuel. Styrene may optionally be collected for purification and re-used. Also, the residue from depolymerization will contain a high concentration of phosphoric acid when phosphoric acid is used as the reaction catalyst. The combustion from residue 23 in power house 15 could allow recovery of the phosphoric acid for re-use.

After fractionation, aqueous lactam-containing stream 26 is optionally subjected to oxidizing agent 30 to oxidize residual impurities which were not removed by the fractionation column to compounds which can be more easily separated in the subsequent process steps. Oxidizing agent 30 is preferably potassium permanganate, provided at about 25° C. to about 75° C., preferably at about 40° C., but other oxidizing agents are also useful. For example, $H_2O_2$, $K_2Cr_2O_7$, sodium or potassium hypochlorites, perchlorite, and perboric acid are useful. When the oxidizing agent is potassium permanganate, it is preferably supplied at about 1–5 weight percent of the caprolactam, but more may be used, depending on how impure the lactam may be. For example, more potassium permanganate is required for more impure lactam. Manganese dioxide may be filtered out as a by-product of the oxidative treatment.

The oxidized aqueous caprolactam is then concentrated when subjected to concentration step 31. Concentration is preferably accomplished by evaporation at elevated temperature of the water, optionally under reduced pressure. If the oxidation step is skipped, then the concentration step may also be skipped, depending on how efficiently the fractionation in step 25 is performed.

After concentration, concentrated $\epsilon$-caprolactam stream 32 is fed to a vacuum distillation unit for additional purification. The distillation preferably takes place at about 100° C. to about 150° C. under a reduced pressure of less than about 20 mm Hg using an evaporator. As the caprolactam may contain carboxylic acid impurities, it is advantageous to carry out the distillation after adding alkali, for example, about 1% by weight of lime. Epsilon-caprolactam 36 suitable for fiber production is provided after vacuum distillation. Epsilon-caprolactam 36 is useful for all common uses of $\epsilon$-caprolactam, including repolymerization to form nylon carpet fiber.

Figure 3:
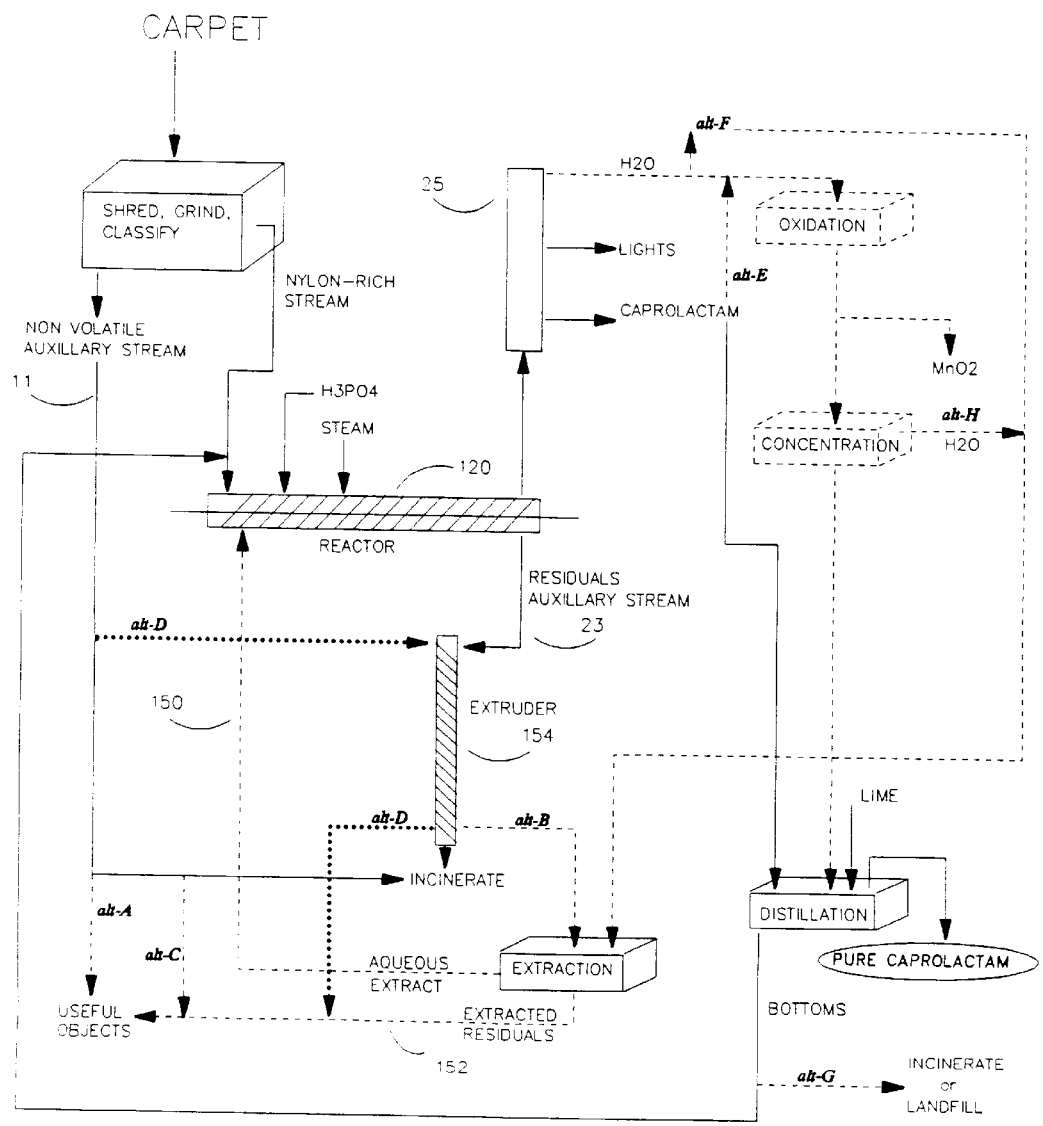
FIG. 3 is a schematic diagram showing alternate uses for auxiliary streams generated from recovering ε-caprolactam.

FIG. 3 illustrates several alternate process pathways for auxiliary streams produced from $\epsilon$-caprolactam recovery. Several methods to upgrade auxiliary streams to product streams are shown. These alternate routings for auxiliary streams are indicated by broken lines.

Instead of incineration, as described above, non-volatile auxiliary stream 11 may be used in several other ways. Alt.-A shows auxiliary stream 11 which for most carpets would contain latex, nylon, polypropylene, and $CaCO_3$ filler. Auxiliary stream 11 may be used directly to form useful objects or may serve as a filler for molding useful objects, rather than being incinerated. Alt.-C shows auxiliary stream 11, which is a $CaCO_3$-rich product, used to neutralize any unextracted $H_3PO_4$ that may be present in extraction residuals 152 (discussed below).

Alt.-D depicts the flow of auxiliary stream 11 to discharging extruder 154. This can be useful when stream 11 contains $CaCO_3$ filler. In extruder 154, $H_3PO_4$ catalyst may be neutralized by the $CaCO_3$ in the latex and a product filled with calcium phosphate together with $CaCO_3$ is made. This product is useful, for example, as a filler in plastics for molding into useful articles.

Alt.-B depicts an alternative to incineration of the residuals from the reactor and to direct re-use of the output from extruder 154. In most cases, residual auxiliary stream 23 from reactor 120 will be rich in polypropylene and $H_3PO_4$. These residuals can be extracted with water to remove the $H_3PO_4$. The $H_3PO_4$ can be recycled back via stream 150 to the reactor to greatly reduce the amount of fresh catalyst needed. In this case, it may be advantageous to concentrate (not illustrated) the acid via evaporation prior to injecting into the reactor.

Obviously, there is little incentive to practice Alt.-D and Alt.-B at the same time. Alt.-B is to be preferred for economic reasons, but Alt.-D may be preferred in some cases if the properties of the materials are especially desired for certain useful articles.

In Alt.-B, residual auxiliary stream 23 is extruded into water, where it remains for a time sufficient to extract all or most of the $H_3PO_4$ or $H_3PO_4$-derived compounds. Aqueous extract 150, which will contain the water soluble catalyst and some residual lactam monomer and oligomers, can be recycled to the feed of the depolymerization reactor. One advantage of using this extraction process is that more $H_3PO_4$ can be used in the reactor without intolerable cost. At the same time, the depolymerization rate is increased due to the higher catalyst concentration. The higher depolymerization rate can be exploited to gain more output or to gain a higher quality lactam by way of lower depolymerization reactor temperatures. Residuals 152 from the extraction can then be pelletized (if not already pelletized before extraction) and used to make useful articles, for example, by adding additional resin, if necessary, and extrusion molding. If necessary, residue 152 can be mixed with basic material to neutralize any remaining add as needed for the desired end use. This is especially useful if polypropylene backing is present, since polypropylene may trap some $H_3PO_4$ and prevent it from being extracted. As discussed with Alt.-C, some or all of non-volatile auxiliary 11 stream can be used for this purpose and also to provide filler.

Alternatively, non-volatile auxiliary stream 11 and residuals auxiliary stream 23 may be combined in extruder 154. The combined waste streams are, typically, non-acidic, having an excess of calcium carbonate. This combined stream is useful for fillers for preparing articles by extrusion molding.

Alt.-F depicts a source of water for the extraction process, fractionating column 25. However, if Alt.-E is used, then the extraction water can be derived from the concentration step Alt.-H. (Alt.-E combines the water and caprolactam condensates from the reactor in order to give the aqueous lactam an oxidation treatment, e.g., with $KMnO_4$, to remove oxidizable impurities.) The bottoms from the final distillation, which contain some impure caprolactam, are recycled back to the reactor to avoid landfilling or incineration (Alt.-G).

The invention will be described by referring to the following detailed examples. These examples are set forth by way of illustration and are not intended to be limiting in scope.

EXAMPLE 1

108 grams of nylon 6 carpet backed with polypropylene and latex are fed to a Schirp separator. Much of the backing material is removed and passed to the feed of a power generator. The nylon portion is charged to a evaporator with 30.0 mL of 85% phosphoric acid. Superheated steam is injected continuously for about 45 minutes. The vapor temperature of the reaction is 250° C.–300° C. The distillate collected (1040 mL) contains 2.9% $\epsilon$-caprolactam (as determined by GC) and thus gives a crude yield of about 56%.

The solids from the reactor are passed to the feed of a power generator. The emissions of the generator upon burning the solids contain $P_2O_5$, which is reacted with water to regenerate phosphoric acid.

The distillate is passed through a fractionating column where non-aqueous volatiles are removed and routed to the power generator. The fractionated aqueous phase is treated with 1–2% $KMnO_4$ at about 40° C.–50° C. Water is removed by evaporation to concentrate the oxidized aqueous phase. About three grams of $Ca(OH)_2$ is added to the crude lactam and after vacuum distillation, nearly pure $\epsilon$-caprolactam is obtained which is suitable for blending with virgin lactam and repolymerization.

EXAMPLE 2

The procedure of Example 1 is followed, except that the Schirp separator is bypassed. The carpet containing nylon 6 is charged directly, after heating, to the evaporator. Nearly pure ε-caprolactam is obtained which is suitable for re-use in making nylon 6 fiber.

EXAMPLE 3

108 grams of nylon carpet, backed with $CaCO_3$ filled latex and polypropylene, is charged to a 1000 ml three-neck round bottom flask with 6 ml of 85% phosphoric acid. Superheated steam is injected continuously during the 45-minute reaction. The vapor temperature of the reaction is 250° C.–300° C. A distillate of 1065 ml is condensed and collected. The distillate contains 1.9% ε-caprolactam. A small quantity of non-aqueous phase is separated from the distillate. The remaining aqueous phase is treated with 2% $KMnO_4$ at 40° C.–50° C. for two hours. The water is removed by evaporation to produce solid ε-caprolactam. About 4 g. of lime is added, and the solid ε-caprolactam is then distilled under about 1 mm Hg to yield nearly pure ε-caprolactam.

EXAMPLE 4

50 kg of Nylon 6 (N6) carpet, having a composition of 53% N6, 25% $CaCO_3$, 12% polypropylene and 10% styrene-butadiene latex, are fed through a Shred-Tech ST-100 shredder. The shredded material is then fed through a 25 HP Battenfeld Gloucester rotary cutter, with 3/16" holes in the screen. The size reduced "fluff" is then fed through an air classification unit (Georgia Marble G-24 Air Sifter) for separation. 25 kg of primarily oversized backing particles are slung outward and drop into a de-dusting cyclone, while 25 kg of primarily fibrous material is pulled through the classifying wheel into a second collection cyclone.

The 25 kg of primarily fibrous material is fed through a Condux CV30 Plastocompactor to be densified. The densified material is then fed through a Condux CS 300/600 rotary cutter to produce uniform product granulate.

The product granulate is analyzed to have a composition of 84% N6, 7% $CaCO_3$, 5% polypropylene and 4% styrene-butadiene latex.

500 grams of product granulate, produced as described above, is charged to a 1000 ml flask/reactor, which is surrounded with an electrical heating mantle. 70 grams of 85 wt % $H_3PO_4$ is also charged to the reactor and premixed with the granulate. 300° C. superheated steam is injected through a distribution ring at the bottom of the reactor, at a rate of 12 gram/min. The reactor temperature is controlled at 280° C., with the electrical heating mantle. Reactor distillate is collected, once the reactor reaches 220° C., and the reaction is carried out for 120 minutes. The distillate collected averages 17% caprolactam and an overall crude caprolactam yield of 89% based on the nylon content of the feed is obtained.

The water fraction of the reactor distillate is removed with a rotary evaporator, leaving behind 370 grams of crude caprolactam. To the 370 grams of crude caprolactam 18.5 grams of slaked lime is added and the entire mixture is distilled, with a stainless steel metal mesh packed column, at an overhead vapor temperature of 115° C. and a column vacuum pressure of 3 mmHg. 333 grams of distillate product is condensed and collected for a yield of 90%.

To the 333 grams of product from the 1st distillation, 0.35 grams of $H_2SO_4$ is added and the mixture is again distilled with the same packed column and operating conditions described above. 310 grams of distillate product is condensed and collected for a yield of 93%.

The caprolactam distillate, obtained from the second distillation, is analyzed and found to be suitable for blending with virgin caprolactam and subsequent repolymerization to nylon 6 polymer.

EXAMPLE 5

The carpet size reduction and separation procedure described in Example 4 is followed, except that the product granulate is analyzed to have a composition of 73% N6, 20% $CaCO_3$, 4% polypropylene and 3% styrene-butadiene latex.

2.3 kg/hr of the above described product granulate is continuously fed, with a screw feed conveyor, to an oil heated DTB-6 reactor, fabricated by LIST Inc. 0.7 kg/hr of $H_3PO_4$ is injected into the reactor, through the feed flange by which the granulate is also introduced. 300° C. superheated steam is injected at a rate of 3.4 kg/hr, through a bottom port located near the feed side of the reactor. The reactor temperature is controlled at an average temperature of 265° C., with hot oil jacketing. 1.4 kg/hr of reactor distillate is collected, with an average caprolactam concentration of 28%. The average reactor discharge rate is 1.6 kg/hr, producing an overall crude caprolactam yield of 80% based on the nylon content of the granulate.

The reactor distillate concentration and purification procedure is the same as that described in Example 4.

The caprolactam product obtained from the purification procedure is analyzed and found to be suitable for blending with virgin caprolactam and subsequent repolymerization to nylon 6 polymer.

What is claimed is:

1. A process for recovering ε-caprolactam from nylon 6 carpet, comprising:
    a) providing a carpet made from nylon 6 fibers and having a backing containing one or more non-nylon 6 materials of polypropylene, jute, latex and fillers to a mechanical separator to prepare scrap containing both nylon 6 and non-nylon 6 backing materials, and a first auxiliary stream;
    b) feeding the scrap from the separator to a depolymerizing reactor to produce an ε-caprolactam containing distillate and a second auxiliary stream;
    c) separating ε-caprolactam in the distillate from other volatiles therein; and
    d) purifying the ε-caprolactam obtained after separating so that the ε-caprolactam is of sufficient purity for reuse as a starting material for nylon 6 intended for use in carpet fiber.

2. The process of claim 1 wherein the first auxiliary stream is used to form into useful objects.

3. The process of claim 2, further comprising extruding the first auxiliary streams.

4. The process of claim 1 or 2, further comprising combining the first and second auxiliary streams prior to 2 step for extruding.

5. The process of claim 1 wherein said feeding is carried out continuously.

6. The process of claim 1 wherein in the depolymerization reactor, the scrap is subjected to a depolymerization catalyst.

7. The process of claim 6, further comprising extracting the depolymerization catalyst and related compounds from the second auxiliary stream with water, leaving water insoluble residuals.

8. The process of claim 7, further comprising recycling the extracted depolymerization catalyst to feed the depolymerization reactor.

9. The process of claims 6, 7 or 8 wherein the depolymerization catalyst is phosphoric acid.

10. The process of claim 7, further comprising supplying the water for said extracting from said purifying steps.

11. A process for recovering ε-caprolactam from nylon 6 carpet comprising:
   a) providing a carpet made from nylon 6 fibers and having a backing containing one or more non-nylon 6 materials of polypropylene, jute, latex and fillers to a mechanical separator to prepare scrap containing both nylon 6 and non-nylon 6 backing materials, and a first auxiliary stream;
   b) feeding the scrap from the separator to a depolymerization reactor wherein the scrap is exposed to a depolymerization catalyst to produce an ε-caprolactam containing distillate and a second auxiliary stream;
   c) separating ε-caprolactam in the distillate from other volatiles therein; and
   d) purifying the ε-caprolactam obtained after separating so that the purified ε-caprolactam is suitable for use as a starting material for nylon 6 carpet fiber;
   e) recovering the depolymerization catalyst from the second auxiliary stream, leaving a residue.

12. The process of claim 11 wherein said recovering is by extraction with water.

13. The process of claims 11 or 12, further comprising recycling the depolymerization catalyst to feed the depolymerization reactor.

14. The process of claims 11, 12 or 13 wherein the depolymerization catalyst is phosphoric acid.

* * * * *